(12) United States Patent
Mark

(10) Patent No.: US 7,390,306 B2
(45) Date of Patent: Jun. 24, 2008

(54) VACUUM ASSISTED BIOPSY NEEDLE SET

(75) Inventor: Joseph L. Mark, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 214 days.

(21) Appl. No.: 10/964,959

(22) Filed: Oct. 14, 2004

(65) Prior Publication Data

US 2005/0080355 A1 Apr. 14, 2005

Related U.S. Application Data

(60) Provisional application No. 60/510,866, filed on Oct. 14, 2003.

(51) Int. Cl.
*A61B 10/00* (2006.01)

(52) U.S. Cl. .................. 600/566; 600/565; 600/567

(58) Field of Classification Search .......... 600/562–572
See application file for complete search history.

(56) References Cited

U.S. PATENT DOCUMENTS

| | | | |
|---|---|---|---|
| 2,472,116 A | 6/1949 | Maynes |
| 2,660,342 A | 11/1953 | Ruf |
| 2,735,427 A | 2/1956 | Sullivan |
| 2,863,452 A | 12/1958 | Ogle, Sr. |
| 2,892,457 A | 6/1959 | Sturtz |
| 3,477,423 A | 11/1969 | Griffith |
| 3,517,688 A | 6/1970 | Scholle |
| 3,561,429 A | 2/1971 | Jewett et al. |
| 3,819,091 A | 6/1974 | Hollender |
| 3,844,272 A | 10/1974 | Banko |
| 3,905,365 A | 9/1975 | Colombo |
| 4,301,802 A | 11/1981 | Poler |
| 4,461,305 A | 7/1984 | Cibley |
| 4,570,632 A | 2/1986 | Woods |
| 4,594,073 A | 6/1986 | Stine |
| 4,600,014 A | 7/1986 | Beraha |
| 4,605,011 A | 8/1986 | Naslund |

(Continued)

FOREIGN PATENT DOCUMENTS

CH        SU 1551362        1/1987

(Continued)

OTHER PUBLICATIONS

International Search Report No. PCT/US2004/033909 dated May 18, 2005.

(Continued)

*Primary Examiner*—Charles A. Marmor, II
*Assistant Examiner*—Rene Towa
(74) *Attorney, Agent, or Firm*—Rader, Fishman & Grauer, PLLC

(57) ABSTRACT

A needle set for a biopsy device is disclosed. The needle set includes an outer member, a cylinder lumen within said outer member, an inner member having a cannula and an inner lumen. The inner member is slidably disposed within the cylinder lumen. The biopsy device also includes a cylinder seal member that is disposed within the cylinder lumen and a cannula seal member attached to the outer surface of the cannula. The cylinder seal member and the cannula seal member define a vacuum chamber therebetween.

17 Claims, 11 Drawing Sheets

U.S. PATENT DOCUMENTS

| | | |
|---|---|---|
| 4,667,684 A | 5/1987 | Leigh |
| 4,708,147 A | 11/1987 | Haaga |
| 4,711,250 A | 12/1987 | Gilbaugh, Jr. et al. |
| 4,733,671 A | 3/1988 | Mehl |
| 4,735,215 A | 4/1988 | Goto et al. |
| 4,747,414 A | 5/1988 | Brossel |
| 4,776,346 A | 10/1988 | Beraha et al. |
| 4,776,840 A | 10/1988 | Freitas et al. |
| 4,781,700 A | 11/1988 | Vicario |
| 4,817,631 A | 4/1989 | Schnepp-Pesch et al. |
| 4,881,551 A | 11/1989 | Taylor |
| 4,893,635 A | 1/1990 | de Groot et al. |
| 4,907,598 A | 3/1990 | Bauer |
| 4,950,265 A | 8/1990 | Taylor |
| 4,982,739 A | 1/1991 | Hemstreet et al. |
| 5,019,036 A | 5/1991 | Stahl |
| 5,025,797 A | 6/1991 | Baran |
| 5,048,538 A | 9/1991 | Terwilliger et al. |
| 5,133,360 A | 7/1992 | Spears |
| 5,159,933 A | 11/1992 | Hut |
| 5,172,701 A | 12/1992 | Leigh |
| 5,183,052 A | 2/1993 | Terwilliger |
| 5,188,118 A | 2/1993 | Terwilliger |
| 5,213,110 A | 5/1993 | Kedem et al. |
| 5,220,926 A | 6/1993 | Jones |
| 5,224,470 A | 7/1993 | Schnepp-Pesch et al. |
| 5,246,011 A | 9/1993 | Caillouette |
| 5,249,582 A | 10/1993 | Taylor |
| 5,282,476 A | 2/1994 | Terwilliger |
| 5,348,022 A | 9/1994 | Leigh et al. |
| 5,400,798 A | 3/1995 | Baran |
| 5,425,376 A | 6/1995 | Banys et al. |
| 5,469,860 A | 11/1995 | De Santis |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,560,373 A | 10/1996 | De Santis |
| 5,649,547 A | 7/1997 | Ritchart et al. |
| 5,769,086 A | 6/1998 | Ritchart et al. |
| 5,775,333 A | 7/1998 | Burbank et al. |
| 5,797,907 A | 8/1998 | Clement |
| 5,817,033 A | 10/1998 | DeSantis et al. |
| 5,928,164 A | 7/1999 | Burbank et al. |
| 5,944,673 A | 8/1999 | Gegoire et al. |
| 5,971,939 A | 10/1999 | DeSantis et al. |
| 5,980,469 A | 11/1999 | Burbank et al. |
| 5,980,545 A | 11/1999 | Pacala et al. |
| 6,017,316 A | 1/2000 | Ritchart et al. |
| 6,019,733 A | 2/2000 | Farascioni |
| 6,050,955 A | 4/2000 | Bryan et al. |
| 6,142,955 A | 11/2000 | Farascioni et al. |
| 6,155,989 A * | 12/2000 | Collins ................... 600/565 |
| 6,193,673 B1 | 2/2001 | Viola et al. |
| 6,387,057 B1 | 5/2002 | Heske |
| 6,428,486 B2 | 8/2002 | Ritchart et al. |
| 6,436,054 B1 | 8/2002 | Viola et al. |
| 6,488,636 B2 | 12/2002 | Bryan et al. |
| 6,551,255 B2 | 4/2003 | Van Bladel et al. |
| 6,554,778 B1 | 4/2003 | Fleming, III |
| 6,554,779 B2 | 4/2003 | Viola et al. |
| 6,589,240 B2 | 7/2003 | Hinchliffe |
| 6,758,824 B1 * | 7/2004 | Miller et al. ............. 600/568 |
| 2002/0082519 A1 * | 6/2002 | Miller et al. ............. 600/566 |
| 2003/0125639 A1 | 7/2003 | Fisher et al. |
| 2003/0195436 A1 | 10/2003 | Van Bladel et al. |
| 2005/0027210 A1 * | 2/2005 | Miller ...................... 600/567 |

FOREIGN PATENT DOCUMENTS

| | | |
|---|---|---|
| DE | 1160573 | 1/1964 |
| DE | 141 108 | 4/1980 |
| EP | 0 010 321 | 4/1980 |
| EP | 0561732 | 9/1993 |
| EP | 1520518 A2 | 4/2005 |
| WO | WO 83/03343 | 10/1983 |
| WO | WO-9624289 A | 8/1996 |
| WO | WO02/22023 A1 | 3/2002 |
| WO | WO-2005037106 A | 4/2005 |
| WO | WO-2005063126 A | 7/2005 |

OTHER PUBLICATIONS

Partial International Search No. PCT/US2004/033909 dated Mar. 8, 2005.

Continue to Provide Opportunities for Innovative Manufacturers by Keith Hammond, dated Apr. 22, 1998.

* cited by examiner

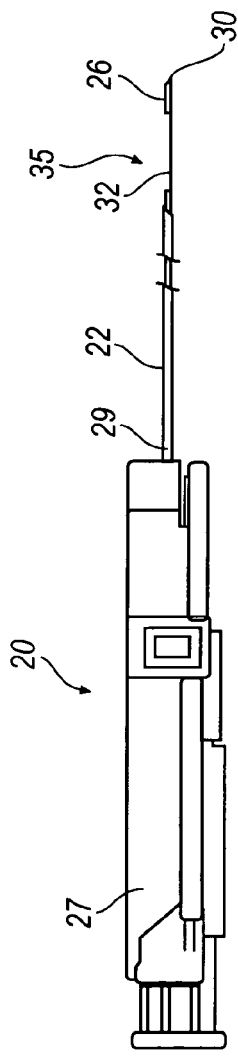
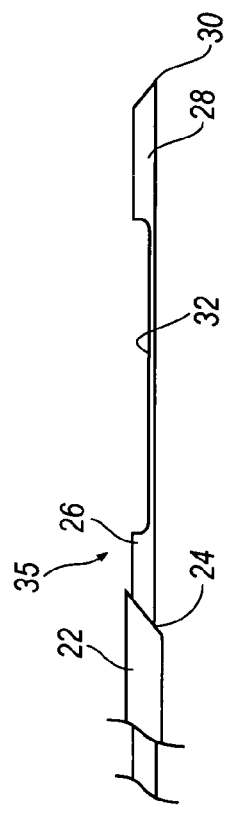
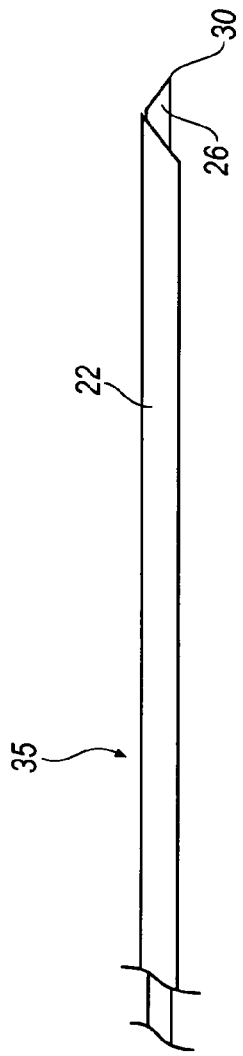
FIG. 1 (PRIOR ART)
FIG. 2 (PRIOR ART)
FIG. 3 (PRIOR ART)

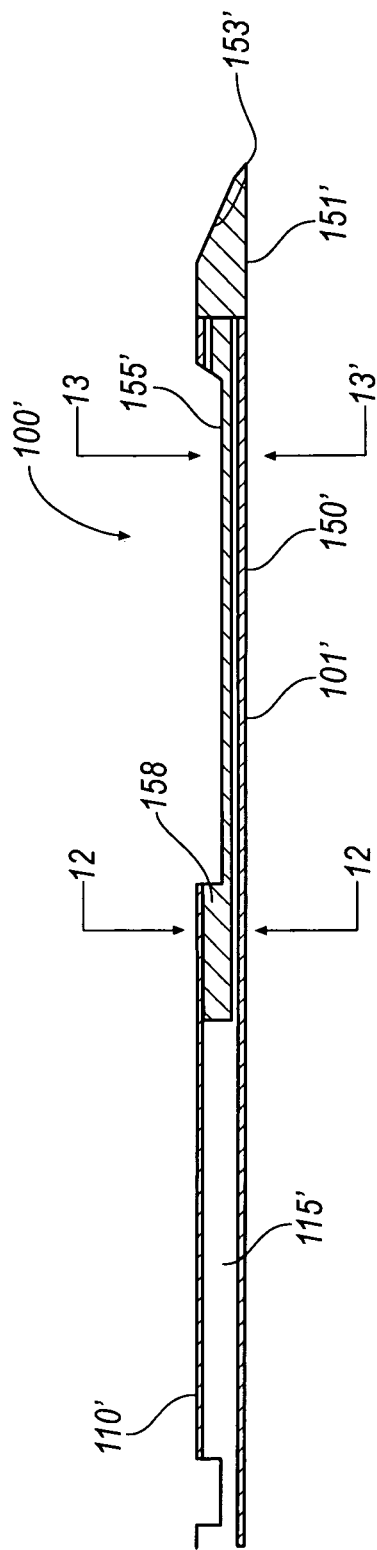
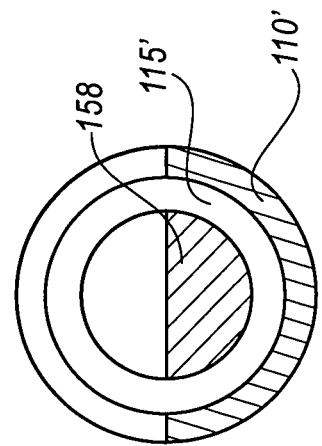
FIG. 11
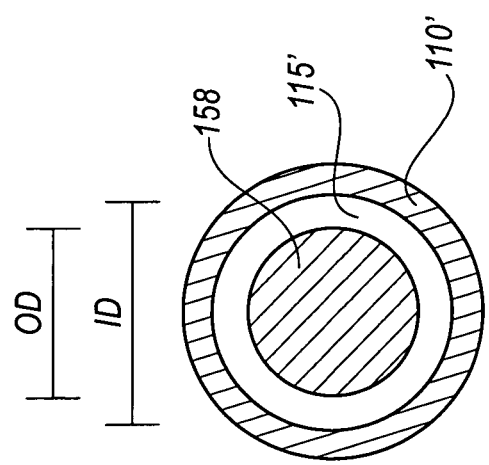
FIG. 12
FIG. 13

VACUUM ASSISTED BIOPSY NEEDLE SET

CROSS REFERENCE TO RELATED APPLICATION

This application claims priority based upon U.S. provisional patent application Ser. No. 60/510,866 filed on Oct. 14, 2003, which is incorporated herein by reference in its entirety.

FIELD OF THE INVENTION

The present invention generally relates to the field of tissue sampling and harvesting. More specifically, the invention relates to biopsy needle sets.

BACKGROUND OF THE INVENTION

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set, which typically includes a stylet with a pointed tip and a notch defined near its distal end. The stylet is slidably disposed within a cannula so that the notch can be alternately exposed or covered. Typically, a hub is connected to the proximal end of each needle. Such needle sets are used with or incorporated in various forms of biopsy devices, such as the single action and double action biopsy devices that are available from Promex/US Biopsy, LLC, 3049 Hudson Street, Franklin, Ind. 46131, (317) 736-0128. For example, such a needle set is incorporated into the single action biopsy device shown in FIGS. 1-4.

Referring to FIGS. 1-4, single action biopsy device 20 includes an outer hollow needle 22 defining a lumen 24 therethrough. A stylet 26 is slidingly disposed within lumen 24 and is moveable relative to outer needle 22. A first or distal end 28 of stylet 26 is provided with a tissue cutting-point 30 and a cavity 32 adjacent to first end 28 for receiving tissue samples. Stylet 26 is slidable relative to outer needle 22 between a first or retracted position (FIG. 3) and a second or extended position (FIG. 2).

In the first position, stylet 26 is retracted within lumen 24 so that outer needle 22 covers cavity 32. In the second position, the first end 28 of stylet 26 is extended away from outer needle 22 to expose cavity 32 to tissues at the biopsy site.

During a biopsy procedure, device 20 will be positioned with the cavity 32 at the targeted site for the biopsy. Stylet 26 is momentarily driven into the tissue far enough to expose cavity 32. Tissue then prolapses into cavity 32. The device is then fired to advance outer needle 22 along stylet 26 to cover cavity 32. This forward movement of outer needle 22 severs the prolapsed tissue to obtain a tissue sample, which becomes trapped in cavity 32 of stylet 26. With outer needle 22 blocking the opening of cavity 32, biopsy device 20 is then withdrawn from the target site, carrying the sample within cavity 32. To collect the biopsy sample, outer needle 22 is once again retracted to expose cavity 32 of stylet 26. The procedure may be repeated several times until satisfactory samples have been obtained.

The firing mechanism for such single action biopsy devices is shown in FIG. 4. Biopsy device 20 is provided with a firing mechanism 40, which includes a housing 27 having finger grips 41 and 42. An actuator 43 is operatively engaged with both the stylet 26 and outer needle 22. Actuator 43 includes a gripping portion 44 and a drive mechanism 45. Drive mechanism 45 operates to depress a drive carriage 46 against the action of a spring 35. Housing 27 includes a resilient latch 36 that engages an underside 47 of the carriage 46 in the retracted position. Latch 36 is released by forward movement of the drive mechanism 45 so that the spring 35 urges carriage 46 outwardly, which in turn thrusts outer needle 22 over the sampling cavity 32 of the stylet 26. Cover 49 snap-fits over housing 27 to protect spring 35 and the sliding engagement between carriage 46 and housing 27 from debris and interference.

Double action biopsy devices also employ similar needle sets. In a double action biopsy device, movement of inner and outer needles 26, 22 to capture a sample occurs almost instantaneously by means of a firing mechanism engaged with proximal ends 29 of needles 26, 22. A double action biopsy device is disclosed in U.S. Pat. No. 5,538,010 to Darr and Ireland.

While these single and double action biopsy devices are widely used, a basic problem remains in the field of biopsy, which is the need to obtain a sufficient amount of sample tissue. One potential cause of the problem is that as the outer needle passes over the tissue cavity, the outer needle has a tendency to push the tissue away from the cavity. This results in samples that are inferior in quality or too small, which precludes the pathologist from conclusively determining whether disease is present, and if so, to what extent it has progressed. The pathologist must then issue an inconclusive diagnostic report. This causes the physician to recall the patient and attempt another needle biopsy, or in some situations, the patient is scheduled for a more invasive, traumatic and expensive procedure such as an open surgical biopsy.

The challenge has been to consistently obtain sufficient tissue volume and quality tissue cores, regardless of tissue type, to meet the needs of the pathologist so that a conclusive diagnosis can be achieved. Therefore, a need remains for advice that can consistently achieve this result.

SUMMARY

The present invention provides a needle set for a biopsy device having an inner member and an outer member, in which the outer member includes a cylinder lumen with a cylinder seal member disposed therein. The inner member includes a cannula, an inner lumen, and a sampling portion. The inner member is slideably disposed within the cylinder lumen through the cylinder seal member. A cannula seal member is engaged with an outer surface of the cannula. The cylinder seal member and cnnula cooperate to define a vacuum chamber. The movement of the outer cannula to a distal position generates vacuum which is delivered to the inner cannula lumen, thereby creating vacuum in the sampling portion of the inner member. The vacuum created in the sampling portion securely retains tissue samples, resulting in more reliable sampling and larger sample volumes.

BRIEF DESCRIPTION OF DRAWINGS

FIG. 1 is a side elevational view of a prior art biopsy device;

FIG. 2 is an enlarged fragmentary view of the device of FIG. 1, showing details of the tip of the device when in an extended position;

FIG. 3 is an enlarged fragmentary view of the device of FIG. 1 showing details of the tip when in a retracted position;

FIG. 11 is a side sectional view of the distal end of another embodiment of a needle set according to an embodiment of the present invention;

FIG. 12 is a cross sectional view of the needle set of FIG. 11 taken along line 12-12 of FIG. 11.

FIG. 13 is a cross sectional view of the needle set of FIG. 11 taken along line 13-13.

Figure 4:
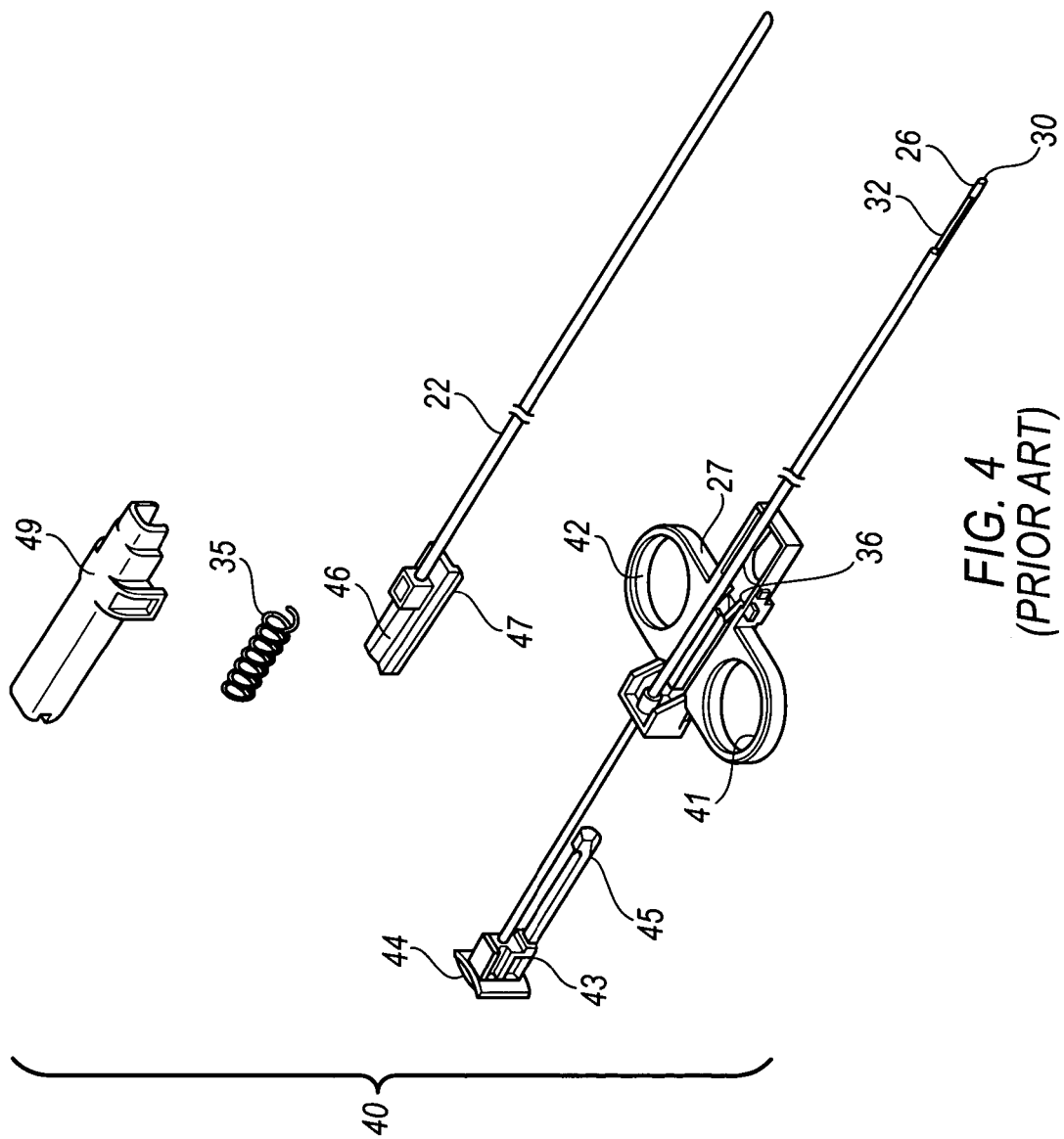
FIG. 4 is an exploded view of the device of FIGS. 1-3.

Although the drawings represent embodiments of the present invention, the drawings are not necessarily to scale and certain features may be exaggerated in order to better illustrate and explain the present invention. The exemplification set out herein illustrates certain embodiments of the invention, in one, or more forms, and such exemplifications are not to be construed as limiting the scope of the invention in any manner.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The terms proximal and distal as used herein will be understood to describe opposite ends of a device or element, and generally will be employed so that proximal is understood as "toward the heart" and distal is understood to mean "away from the heart" or "away from the practitioner" and "toward the practitioner," respectively.

FIGS. 5-10 depict a needle set 50 for a biopsy device made in accordance with the present invention. Needle set 50 includes an inner member 100 slidably disposed within a lumen of an outer member 60. Outer member 60 has a tip member 61 attached to a cylinder portion 70 of outer member 60 and a hub member 80 positioned on the proximal end of outer member 60. Tip member 61 has a working end 63 with an opening 63(a), an opposite end 64 and a tip lumen 65 defined therebetween. As seen most clearly in FIG. 6, cylinder portion 70 has a first end 71 hermetically connected to the opposite end 64 of the tip member 61 and a second end 73. A cylinder lumen 75 is defined between first and second end 71 and 73. The cylinder lumen 75 is in fluid communication with the tip lumen 65. Hub member 80 is positioned on the second end 73 of the cylinder. Hub member 80 defines a hub lumen 85 in fluid communication with the cylinder lumen 75. The hub lumen 85 is also in fluid communication with a pair of openings 86a, 87a defined in opposite sides 86, 87 of the hub member 80. A vent seal 88 is disposed within the hub member 80. The second end 73 of the cylinder portion 70 is attached to hub member 80 at one of the opposite sides 86 and positioned so that the cylinder lumen 75 is aligned with the hub lumen 85.

A cylinder seal member 90 is positioned within the cylinder lumen 75 and fixed to the interior surface of the cylinder 70. The cylinder seal member 90 is any suitable seal member, such as for example, an O-ring. Cylinder seal member 90 defines an opening 91, which is in communication with the cylinder lumen 75.

Figure 5:
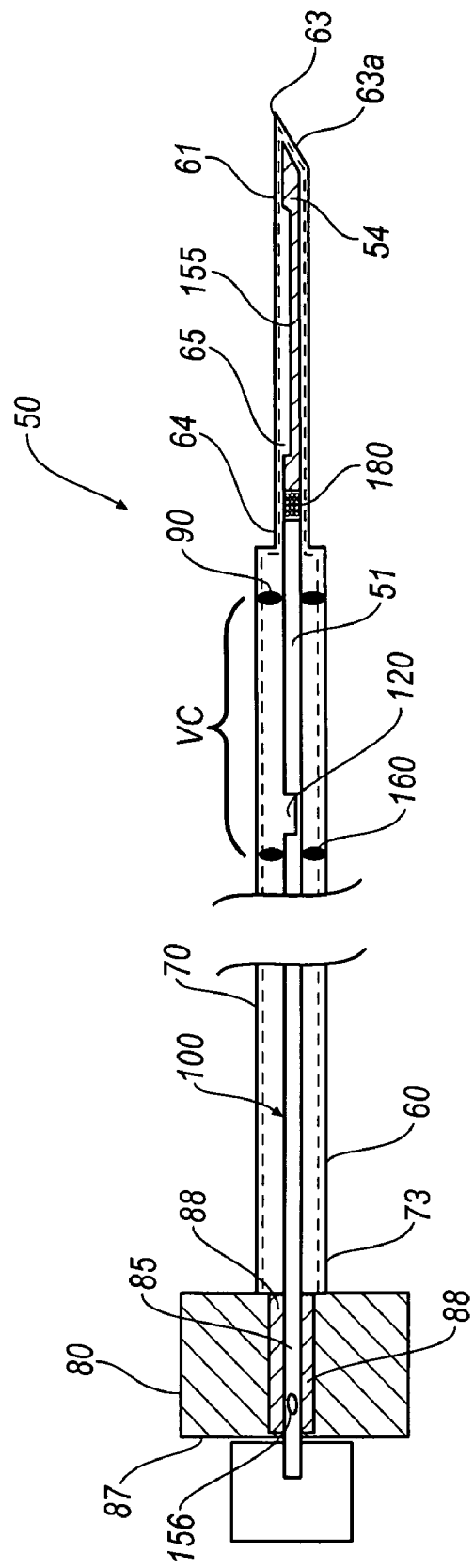
FIG. 5 is a partial sectional view showing a needle set havng an outer member and an inner member according to an embodiment of the present invention.
Figure 6:
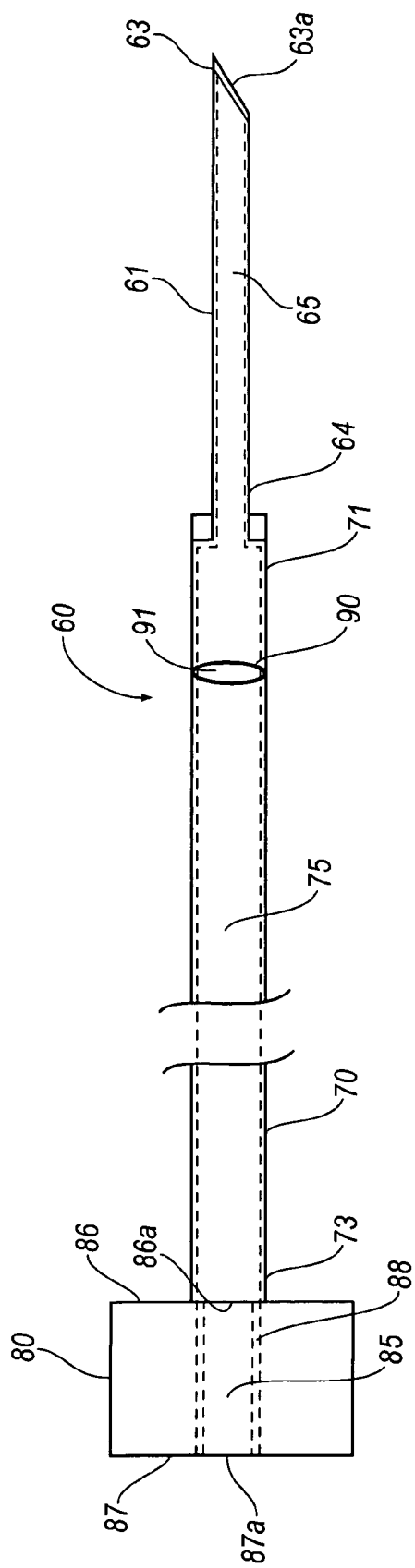
FIG. 6 is a side elevational view of an outer member of the needle set of FIG. 5.
Figure 7:
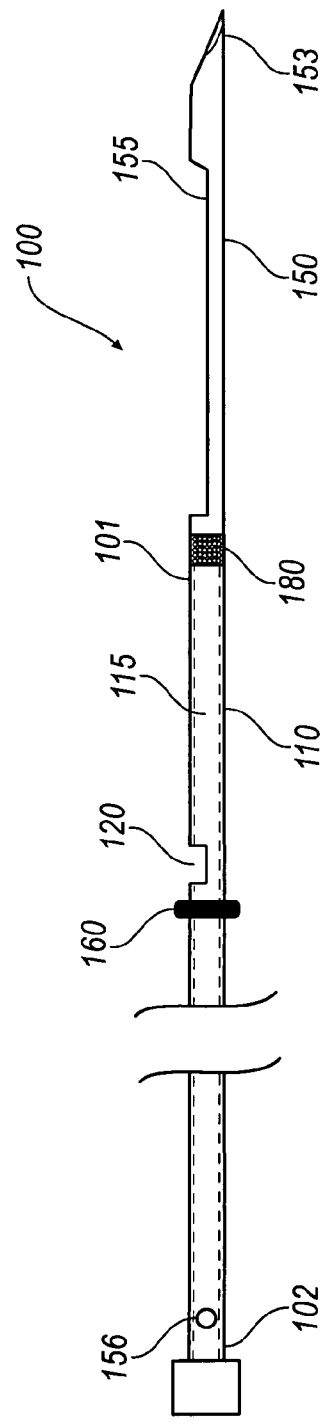
FIG. 7 is a side elevational view of an inner member of the needle set of FIG. 5.

Referring now to FIG. 7, inner member 100 includes a cannula 110 and a sampling portion 150. Cannula 110 may be slidably disposed within the cylinder lumen 75 and through the opening 91 of the cylinder seal member 90 as shown in FIG. 5. An inner lumen 115 is defined between the distal and proximal ends 101, 102. Cannula 110 defines an opening 120 and a vent aperture 156 adjacent the proximal end 102. Both the opening 120 and vent aperture 156 are defined through the wall of the cannula 110 and are in fluid communication with the inner lumen 115. While opening 120 is shown as a notch, it is understood that opening 120 may take the form of other configurations without departing from the invention.

Sampling portion 150 is attached to the distal end 101 of cannula 110. Sampling portion 150 defines a sampling cavity 155. Sampling portion 150 may also be provided with a tissue piercing tip 153. A cannula seal member 160 is fixed to the outer surface of the cannula 110 proximal to the opening 120. Cannula seal member 160 is configured to movably seal within the cylinder lumen 75 of FIG. 6.

Figure 8:
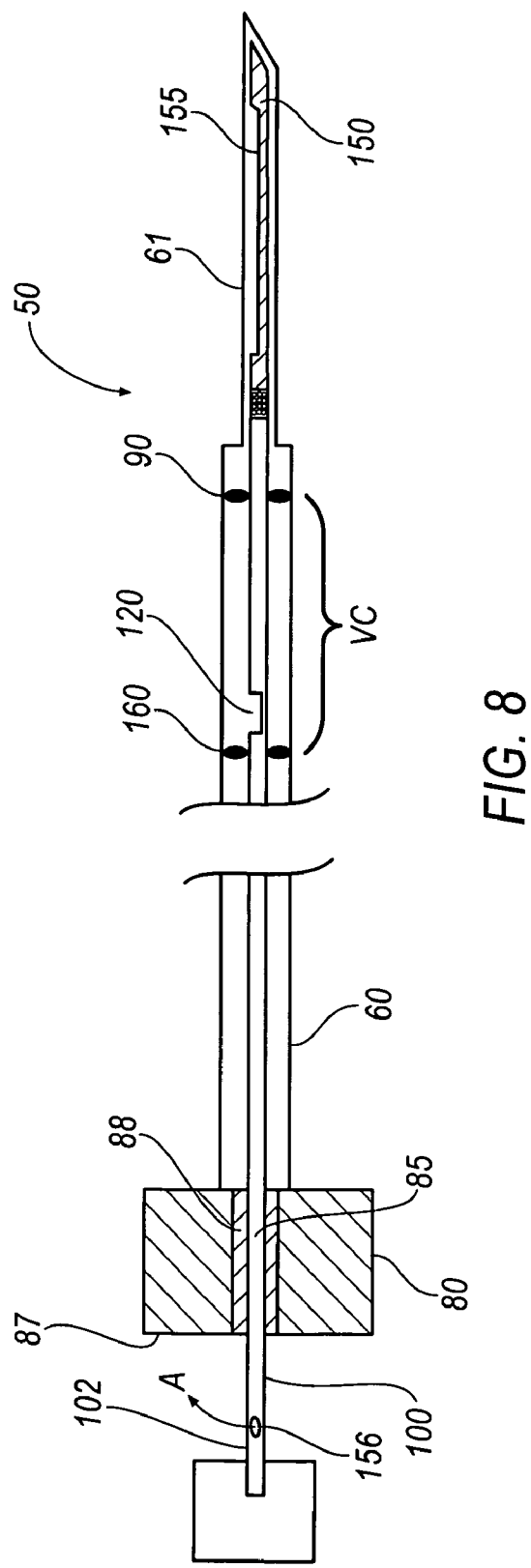
FIG. 8 is a partial side sectional view of the needle set in a first or retracted position.
Figure 9A:
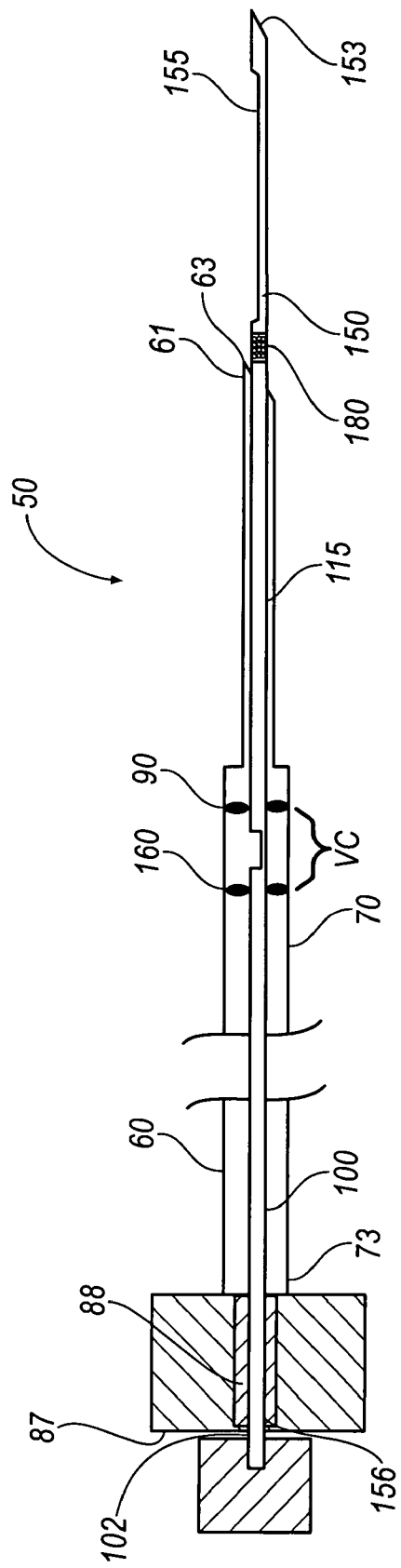
FIGS. 9A and 9B are partial side sectional views of the needle set of FIG. 5 in the second or extended position.

As shown in FIG. 8, the cannula seal member 160 and the cylinder seal member 90 cooperate to define a vacuum chamber VC. The opening 120 may be disposed within the vacuum chamber VC. The inner and outer members 60, 100 are movable relative to one another between a retracted position in which the tip member 61 covers the sampling cavity 155 and the vacuum chamber VC is expanded, and an extended position. The needle set may be placed in a cocked position as shown in FIG. 8 with the vent aperture 156 exposed to vent air from the inner lumen 115 as the needle set is moved to the extended position (as shown in FIG. 9A) such that movement of the outer member 60 to the distal position generates vacuum which is delivered to the inner lumen 115. In the extended position the sampling portion 150 is extended away from the tip member 61 to expose the sampling cavity 155 and the vacuum chamber VC is contracted. The vent aperture 156 is sealed by the vent seal 88 when the needle set is completely in the extended position.

Figure 9B:
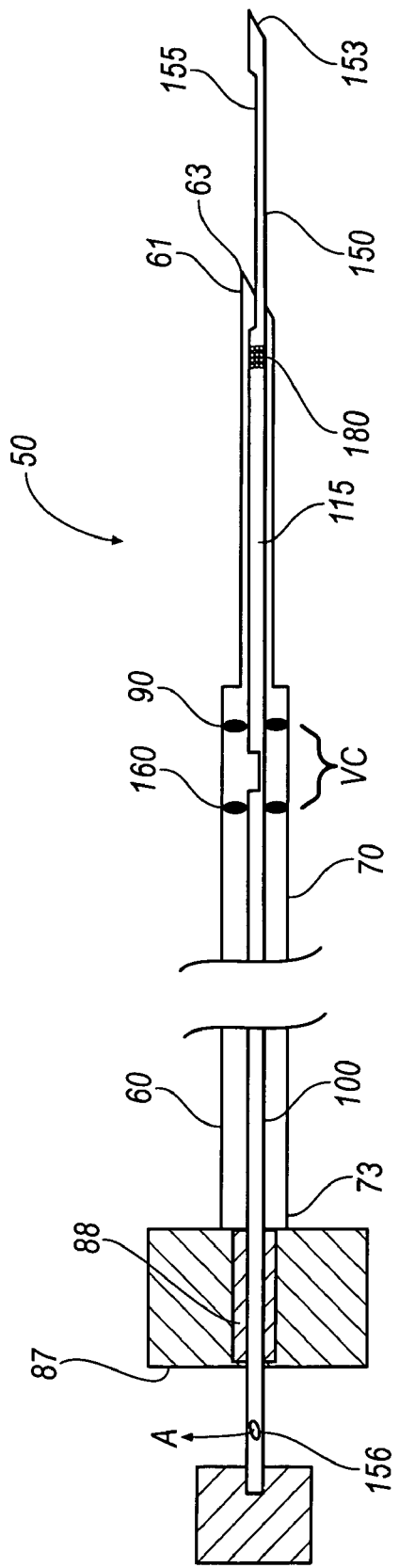
Figure 10:
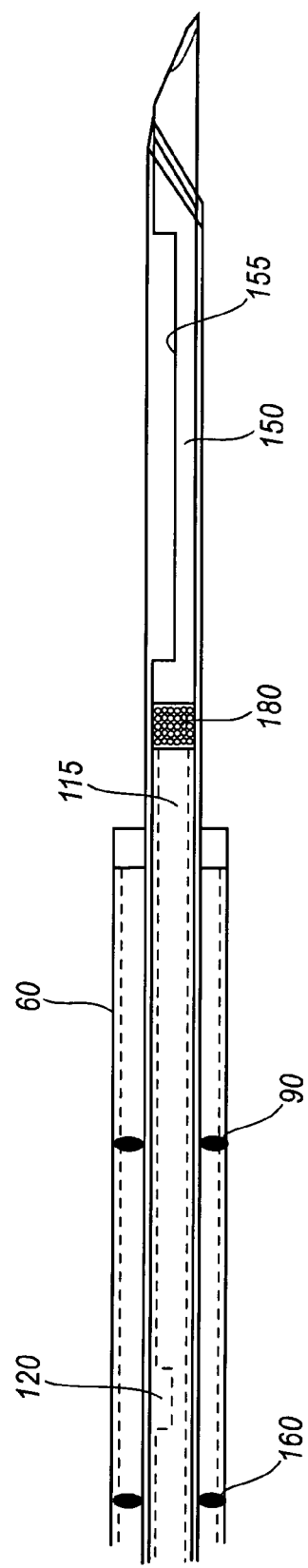
FIG. 10 is an enlarged side elevational view of the distal end of the needle set of FIG. 5.

As the device is cocked, the inner member 100 is pulled towards the operator, which exposes the vent aperture 156 beyond the proximal end 87 of the hub 80 of the outer cannula 60, as shown in FIG. 8. Referring to FIG. 9B, the inner needle 100 is pushed forward to expose the cavity 155 to tissue, the vacuum chamber VC is collapsed, as indicated by the closer proximity between the cannula seal member 160 and the cylinder seal member 90. Accordingly, air is vented out through the vent aperture 156 along the direction of arrow A. The vent aperture 156 is designed to prevent pushing air out though the cavity 155. Firing the device causes the outer member 60 to move distally, which expands the vacuum chamber VC. Expanding the vacuum chamber VC creates a vacuum in the inner lumen 115, which is communicated to the cavity 155 as the vent aperture 156 is sealed within vent sleeve 88 disposed within the hub lumen 85. The vacuum generated in the extended position serves to bias the tissue toward the sampling cavity 155 and hold the tissue in place while the suspect tissue is severed. Therefore, vacuum is applied to the tissue in cavity 155 as the tip member 61 of the outer member 60 moves over the sampling portion 150 of the inner member 100. In contrast, when prior art devices are used, the outer member will push tissue away from the cavity, reducing the size of the sample or requiring multiple attempts to capture the sample. In the embodiments of the present invention, the vacuum created by the enlargement of the vacuum chamber holds the tissue in place within the cavity 155 resulting in more reliable sampling and larger sample volumes.

The needle set may also include a metering mechanism for selectively allowing the exchange of air but not tissue between the cavity 155 and the inner lumen 115. As shown more clearly in FIG. 10, in one particular embodiment, the metering mechanism includes a filter member 180 fitted within the inner lumen 115 or disposed between the inner lumen 115 and the sampling portion 150. Materials suitable for the filter member are commercially available. The selected material should, but not necessarily, have a pore size that allows the exchange of air but is too small for body tissue.

An alternative embodiment of the metering mechanism includes the inner member 110' shown in FIGS. 11-13. The distal tip member 151' of sampling portion 150' includes tissue piercing tip 153' and a solid insert 158. As illustrated by FIGS. 12-13, solid insert 158 has an outer diameter OD less than the inner diameter ID of the inner lumen 115' so that air may pass around the insert 158 when the insert is disposed within the inner lumen 115'. As shown, the insert 158 is substantially centered within the inner lumen 115'. In alternate embodiments, based on design requirements, the insert 158 may be shifted to a particular side or portion of the inner lumen 115' thereby modifying the air flow within the inner lumen 115'. The insert 158 and the inner lumen 115' should be, but not necessarily, dimensioned so that the space between them allows air to pass but not tissue.

Figure 14:
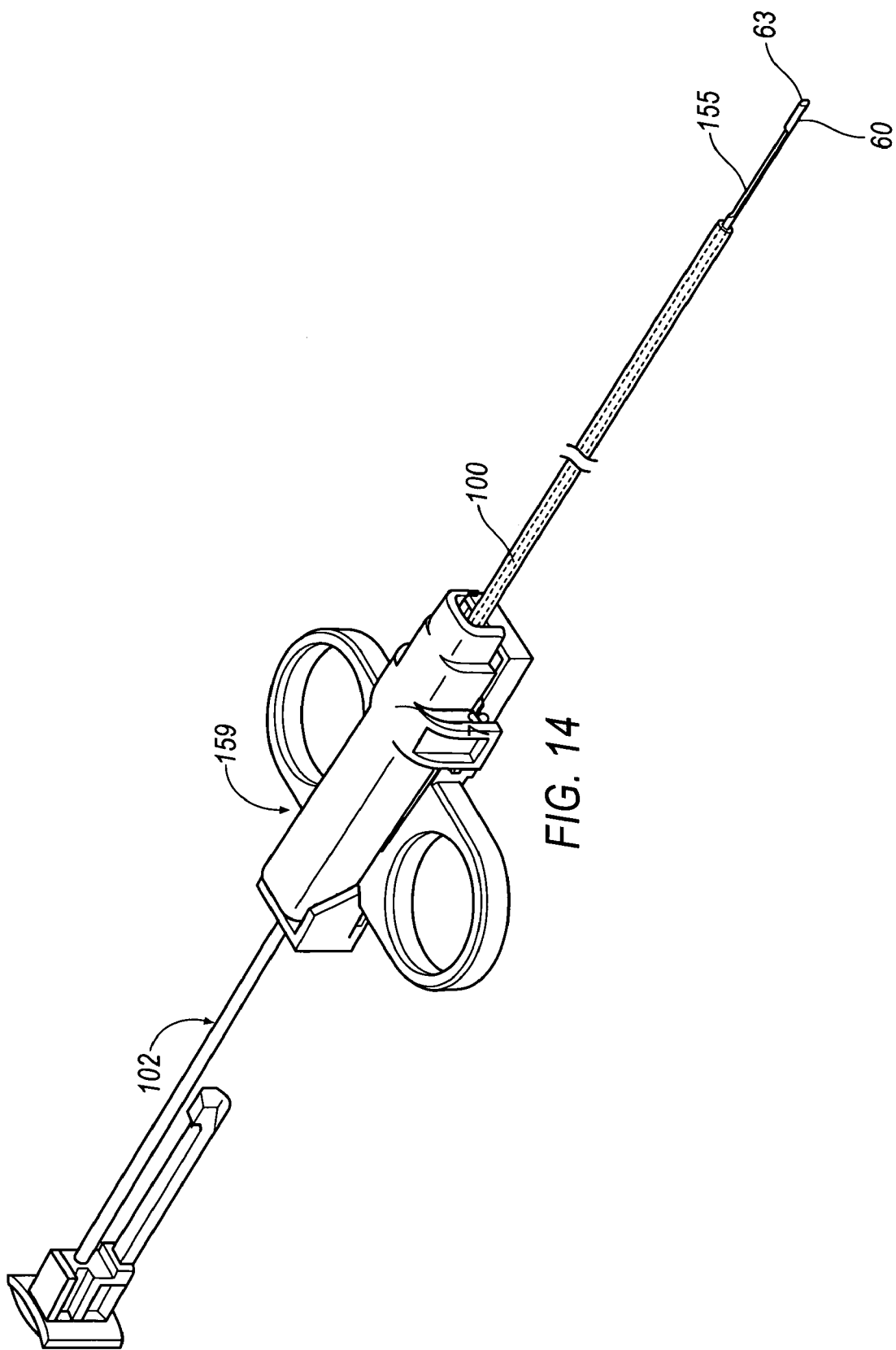
FIG. 14 is a perspective view of the needle set of FIG. 5 having a firing mechanism.
Figure 18:
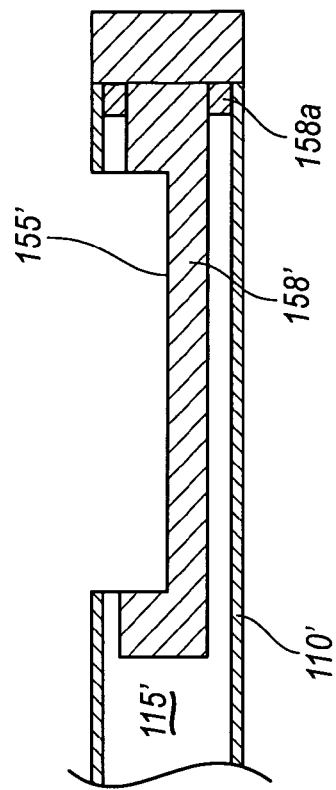
FIG. 18 is a sectional view of a portion of the inner member of FIG. 7.

The needle set embodiments herein may be operated via a biopsy device. For example, the needle set can be loaded into a double action biopsy device or incorporated into a single action biopsy device. FIG. 14 illustrates a needle set including an advancing mechanism 159, operatively engaged to the second end 73 of the cylinder 70 and the proximal end 102 of the inner member 100. The advancing mechanism 159 is operable to move the outer member 60 relative to the inner member 100 from the second position to the first position to trap tissue from the biopsy site in the sampling cavity 155.

Figure 15:
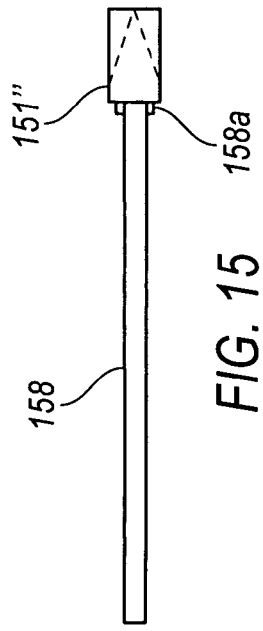
FIGS. 15-17 show the construction of the inner member of FIG. 7.
Figure 16:
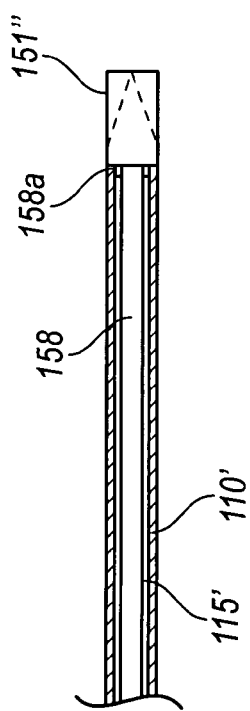
Figure 17:
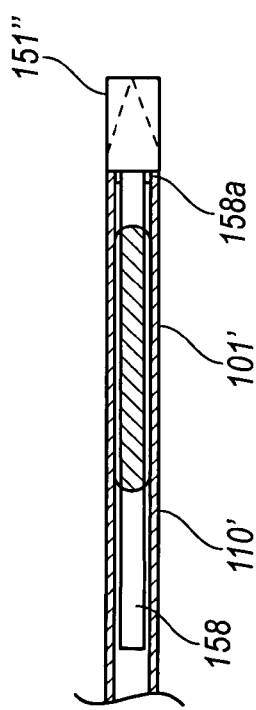

The embodiments of the inner member 100 described herein may be constructed according to the steps depicted in FIGS. 15-18. As shown in FIG. 15, insert 158 may be attached to a connecting element 158a and a blank 151". As shown in FIG. 16, insert 158 is positioned within the lumen 115' of the cannula 110', with the cannula 110' friction fitted to the connecting element 158a. The connecting element 158a could be a ring or a pair of projections, for example. The sampling cavity 155' is then machined through a distal portion 101' of the cannula 110' and into the solid insert 158 to achieve the configuration shown in FIGS. 17-18. The inner member 100 may be inserted into the cylinder lumen 75 of the outer member 60 (as shown in FIG. 8). A tissue piercing tip can be formed at any point in the process, using any suitable methods, such as by machining the blank 151".

The assemblies of this invention can be provided in any suitable shape and size and can be manufactured using any suitable materials. In one particular embodiment, the needle set is composed of surgical grade stainless steel.

Other embodiments of the invention will be apparent to those skilled in the art from consideration of the specification and practice of the invention disclosed herein. It is intended that the specification, drawings and examples be considered as exemplary only, with the true scope and spirit of the invention being indicated by the following claims. It should be understood that the embodiments shown and described and all changes and modifications that come within the spirit of the invention are desired to be protected.

What is claimed is:

1. A needle set for a biopsy device, comprising:
    an outer member having
        a tip member having a working end, an opposite end and a tip lumen defined therebetween;
        a cylinder portion having a first end hermetically connected to said opposite end of said tip member, a second end and a cylinder lumen defined therebetween, said cylinder lumen in fluid communication with said tip lumen;
        a hub member defining a hub lumen in fluid communication with said cylinder lumen, said hub lumen in fluid communication with a pair of openings defined in opposite sides of said hub member;
        said second end of said cylinder attached to said hub member at one of said opposite sides of said hub member and positioned so that said cylinder lumen is aligned with said hub lumen; and
        a cylinder seal member positioned within said cylinder lumen and fixed to an interior surface of said cylinder, said cylinder seal member defining an opening therethrough in communication with said cylinder lumen, and a vent seal disposed within said hub lumen; and
    an inner member having
        a cannula slidably disposed within said cylinder lumen and through said opening of said cylinder seal member and having a proximal end and a distal end with an inner lumen defined therebetween, said cannula further defining a vent aperture adjacent said proximal end of said cannula;
        a sampling portion attached to said distal end of said cannula, said sampling portion defining a sampling cavity;
        a cannula seal member fixed to an outer surface of said cannula proximal to said sampling portion, said cannula seal member configured to movably seal within said cylinder lumen;
    wherein the cannula includes an opening that is disposed between said cylinder seal member and said cannula seal member;
    wherein at least said cannula seal member and said cylinder seal member cooperate to define a vacuum chamber; and
    wherein said inner member and said outer member are movable relative to one another between
        a retracted position in which said tip member covers said sampling cavity and said vacuum chamber is expanded, and
        an extended position wherein said sampling portion is extended away from said tip member to expose said sampling cavity and said cannula seal member is moved away from said cylinder seal member to generate vacuum to bias tissue toward said sampling cavity,
    wherein the generated vacuum selectively increases at the tissue site generally proportionally to the distance that said cannula seal member is moved away from said cylinder seal member; and
    wherein said needle set is operable to be placed in a cocked position with said vent aperture exposed to vent air from the inner lumen as the cannula is moved to the extended position, said vent aperture being sealed by said vent seal when said cannula is in the extended position.

2. A needle set according to claim 1, wherein said sampling cavity has an opening that is transverse to the axis of said cylinder lumen.

3. A needle set according to claim 2, wherein said inner member further includes a piercing tip.

4. A needle set according to claim 1, wherein said vent aperture is disposed opposite said sampling cavity relative to said cannula seal member.

5. A needle set according to claim 1 wherein said hub member is positioned on an end of the outer member, wherein said hub member includes a lumen therethrough, said lumen being in fluid communication with said inner lumen.

6. A needle set according to claim 1, wherein the inner lumen of said inner member includes a porous filter member disposed therein.

7. A needle set according to claim 6, wherein said filter member has a pore size that prohibits the passage of body tissue.

8. A needle set according to claim 1, wherein said sampling portion includes a distal tip and a solid insert having an outer diameter less than an inner diameter of said inner lumen, said sampling portion being engaged with said cannula with said solid insert disposed within a distal end of said inner lumen and said distal tip projecting from said distal end of said cannula, and said sampling cavity being defined through a distal portion of said cannula, and into said solid insert.

9. A needle set according to claim 1, wherein said cylinder seal member is an O-ring.

10. A needle set according to claim 1 further comprising an advancing mechanism engaged to said inner member; said advancing mechanism being operable to move said outer member relative to said inner member.

11. A needle set according to claim 1, further comprising a filter member disposed between said inner lumen and said tip member.

12. A needle set according to claim 1, further comprising an advancing mechanism engaged to said second end of said cylinder and said proximal end of said cannula, said advancing mechanism operable to move said outer member relative to said inner member from the second position to the first position to trap tissue from the biopsy site in the sampling cavity.

13. A needle set according to claim 1, further including an opening disposed between said cylindrical seal member and said cannula seal member.

14. A needle set according to claim 1, wherein said needle set will selectively sever tissue as a vacuum is applied to the tissue.

15. A needle set according to claim 1, wherein said cylinder seal member is moved away from said cannula seal member to increase a vacuum on the tissue.

16. A needle set according to claim 8, wherein the solid insert is centered within inner lumen.

17. A needle set according to claim 16, wherein the insert and the inner lumen are sized such that the clearance path prohibits the passage of body tissue.

\* \* \* \* \*